United States Patent
Davis et al.

(10) Patent No.: US 7,019,165 B2
(45) Date of Patent: Mar. 28, 2006

(54) POLYOXOMETALLATE CATALYSTS AND CATALYTIC PROCESSES

(75) Inventors: Mark E. Davis, Pasadena, CA (US); Christopher J. Dillon, San Rafael, CA (US); Joseph H. Holles, Houghton, MI (US); Jay A. Labinger, Claremont, CA (US); Axel Brait, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/103,205

(22) Filed: Apr. 11, 2005

(65) Prior Publication Data

US 2005/0192461 A1 Sep. 1, 2005

Related U.S. Application Data

(62) Division of application No. 10/286,066, filed on Nov. 1, 2002, now Pat. No. 6,914,029.

(60) Provisional application No. 60/335,316, filed on Nov. 2, 2001, provisional application No. 60/405,575, filed on Aug. 23, 2002.

(51) Int. Cl.
  *C07C 63/14* (2006.01)
  *C07C 63/307* (2006.01)
  *C07C 68/313* (2006.01)
(52) U.S. Cl. .............. 562/480; 562/400; 568/399; 502/208; 502/150; 585/467
(58) Field of Classification Search ........... 568/399; 502/208, 150; 585/467, 10; 562/400, 480
See application file for complete search history.

(56) References Cited

U.S. PATENT DOCUMENTS

| | | | | |
|---|---|---|---|---|
| 5,817,881 A * | 10/1998 | Ellis et al. | ............ | 568/399 |
| 5,990,348 A * | 11/1999 | Lyons et al. | ............ | 562/549 |
| 6,022,986 A * | 2/2000 | Scharbert et al. | ............ | 556/28 |
| 6,060,419 A * | 5/2000 | Wijesekera et al. | ............ | 502/208 |
| 6,124,499 A * | 9/2000 | Hibst et al. | ............ | 562/535 |
| 6,169,202 B1 * | 1/2001 | Wijesekera et al. | ............ | 562/549 |
| 6,335,474 B1 * | 1/2002 | .O slashed.stberg et al. | .. | 208/63 |
| 6,379,586 B1 * | 4/2002 | Zeng et al. | ............ | 252/373 |
| 6,432,867 B1 * | 8/2002 | Kasztelan | ............ | 502/216 |
| 6,447,745 B1 * | 9/2002 | Feeley et al. | ............ | 423/648.1 |
| 6,455,597 B1 * | 9/2002 | Hohn et al. | ............ | 518/715 |
| 6,518,216 B1 * | 2/2003 | Han et al. | ............ | 502/215 |
| 6,710,207 B1 * | 3/2004 | Bogan et al. | ............ | 562/549 |

* cited by examiner

*Primary Examiner*—J. A. Lorengo
*Assistant Examiner*—Jennine Brown
(74) *Attorney, Agent, or Firm*—Wallace L. Oliver; Thomas E. Nemo

(57) ABSTRACT

An active and selective hydrocarbon partial oxidation catalyst comprises an activated partially-reduced polyoxometallate, preferably niobium polyoxomolybdate, that is prepared from a suitable polyoxoanion, which has been exchanged with a suitable cation and activated by heating to an activation effective temperature in the presence of a suitable reducing agent such as pyridinium. $C_3$ and $C_4$ hydrocarbons may be partially oxidized selectively to acrylic acid and maleic acid.

16 Claims, No Drawings

POLYOXOMETALLATE CATALYSTS AND CATALYTIC PROCESSES

CROSS-REFERENCE TO RELATED APPLICATIONS

This application is a division of application Ser. No. 10/286066 filed Nov. 1, 2002, now U.S. Pat. No. 6,914,029 B2.

This application claims the benefit of U.S. Provisional Application No. 60/335,316, filed Nov. 2, 2001, and U.S. Provisional Application No. 60/405,575, filed Aug. 23, 2002, both of which are incorporated by reference herein.

FIELD OF THE INVENTION

This invention relates to oxidation catalysts and processes and particularly to activated polyoxometallate materials that are useful as catalysts in oxidation of hydrocarbons including partial oxidation of alkanes.

BACKGROUND OF THE INVENTION

Conversions of hydrocarbons or substituted hydrocarbons by catalytic reactions such as oxidation are significant commercial processes. A direct catalytic partial oxidation of a hydrocarbon feedstock, such as an alkane or alkene, with high activity and selectivity would be an important process capable of commercial use. The current example of a commercial direct oxidation of an alkane is oxidation of butane to maleic anhydride using a vanadium phosphorus oxide (VPO) catalyst system. There is an ongoing need for new and improved processes to produce acrylic acid and maleic acid by partial oxidation of inexpensive feedstocks such as propane and butane.

A desirable catalyst system and process would operate at relative low temperatures and pressures with high catalyst productivity and selectivity.

Heteropolyacids have been widely described as oxidation catalysts, such as to oxidize alkanes to unsaturated carboxylic acids. Further, heteropolyacids substituted with a wide variety of elements have been described generally as catalysts for oxidation and other purposes. Polyoxometallates and heteropolyacids are described in Pope et al., *Heteropoly and Isopoly Oxometallates: Inorganic Chemistry Concepts*, Springer-Verlag, New York (1983) (ISBN: 0387118896), incorporated herein by reference. Pope et al. and others have described numerous uses of heteropolyacids ("HPA's") and polyoxometallates ("POM's") in catalysis such as oxidation of propylene and isobutylene to acrylic and methacrylic acids, oxidation of aromatic hydrocarbons; olefin polymerization; ammoxidation; oxidation of crotonaldehyde or butadiene to furan; dehydration of alcohols; oxidative coupling of alkyl benzenes or heterocycles; epoxidation; and hydrodesulfurization.

Ueda and co-workers ("Partial Oxidation of Propane to Acrylic Acid over Reduced Heteropolymolybdate Catalysts," *Chemistry Letters* 1995, pp. 541–542 (1995); "Catalytic performance for propane selective oxidation and surface properties of 12-molybdophosphoric acid treated with pyridine," *Applied Catalysis A: General*, vol. 182, pp. 357–363 (1999)) have described partial oxidation of propane to acrylic acid using a heteropolymolybdophosphoric acid treated with pyridine and heated in the catalyst preparation. However, the Ueda et al. catalyst and process have been found to have relatively low activity with limited catalyst lifetimes.

Examples of heteropolyacids and polyoxometallates incorporating a wide variety of elements and other constituents and used in catalyst systems include U.S. Pat. Nos. 5,990,348, 6,060,419, and 6,060,422, 6,169,202. Examples of other mixed metal oxide catalyst systems include U.S. Pat. Nos. 5,380,933 and 6,294,685.

The abundance and low cost of light alkanes has motivated the search for new catalytic materials that can accomplish selective oxidation processes. The conversion of n-butane to maleic anhydride over V—P—O catalysts with molecular oxygen is commercially well established. Other reactions of current interest are the production of acetic acid from ethane and acrylic acid from propane. Polyoxometallates are among the numerous catalytic materials that have been investigated for each of the aforementioned reactions. Typically, different polyoxometallate compositions have been used for each alkane. These compounds (and other mixed metal oxides) have not been found to perform as well as V—P—O catalysts for the conversion of n-butane to maleic anhydride, or as well as mixed metal oxides containing Mo—V—Nb—Te or Mo—V—Nb—Sb for conversion of propane to acrylic acid.

We have discovered a new catalyst system that achieves selective oxidation of both n-butane and propane. Li et al. (*Appl. Catal. A.*, vol. 182, pp. 357–363 (1999)) have reported that a solid obtained by treating molybdophosphoric acid, $H_3PMo_{12}O_{40}$ (denoted as $PMo_{12}$) with pyridine followed by activation in nitrogen at 420° C. exhibits catalytic activity for oxidation of propane to acrylic acid. Ueda et al. also showed that molybdovanadophosphoric acid ($PMo_{11}V$) similarly treated gives a less active and selective catalyst. Our preferable catalysts are obtained from $PMo_{12}$ and $PMo_{11}V$, exchanged sequentially with niobium oxalate (giving $NbPMo_{12}$ and $NbPMo_{11}V$) and pyridine (giving $NbPMo_{12}pyr$ and $NbPMo_{11}Vpyr$) in aqueous media, followed by heating in flowing non-oxidizing atmosphere.

Catalysts of this invention exhibit substantially higher productivities (in terms of space time yield (STY)) and at least comparable selectivities, as well as the ability to operate efficiently at lower temperatures (~300° C.). In addition to hydrocarbon-rich conditions, these new catalysts perform well in more typically-studied hydrocarbon-lean environments (e.g., $C_4/O_2=1/10$).

These new catalysts are effective for more than one feedstock. Propane also may be oxidized selectively to a variety of partially oxidized products. Interestingly, in addition to forming acrylic and acetic acids, respectively, the catalyst produces substantial amounts of maleic acid.

Although catalytic uses of heteropolyacids have been described widely, there is a need for catalyst materials that are capable of partial oxidation of hydrocarbons and other compounds under relatively mild conditions at high activity. Applicants have discovered an effective catalyst material based on a suitable Group 3–15 or lanthanide metal salt of a polyoxoanion that has been activated by partial reduction and phase transformation. This catalyst material is capable of oxidizing an alkane such as propane or butane to acrylic or maleic acids with high activity and selectivity.

SUMMARY OF THE INVENTION

An active and selective hydrocarbon oxidation catalyst comprises an activated partially-reduced Group 3–15 or lanthanide metal polyoxometallate, preferably niobium polyoxomolybdate. Such a catalyst is prepared from a suitable polyoxoanion, preferably a heteropolyacid anion containing molybdenum, and optionally vanadium, in the polyoxoanion cage, which has been exchanged preferably with niobium and activated by heating to an activation effective temperature in the presence of a suitable reducing agent. Preferably, pyridinium added to the niobium polyoxomolybdate acts as an effective reducing agent during activation.

In another aspect of this invention, hydrocarbons are oxidized to partially oxidized products using the catalysts of this invention. For example, propane and butane may be partially oxidized to acrylic acid and maleic acid using these catalysts.

DESCRIPTION OF THE PREFERRED EMBODIMENT(S)

Pope et al. describe heteropolyacids and polyoxometallates as molecular structures typically containing one or more central "heteroatoms" surrounded by a cage framework of metal atoms bonded to oxygen atoms. In a typical heteropolyacid or polyoxometallate, a suitable heteroatom ("X") typically is tetrahedrally bonded to the framework metal atoms ("M") through oxygen atoms ("O"). The framework metals typically are bonded to a central X atom octahedrally through oxygen atoms and are bonded further to other framework M metals through oxygen atoms. The M metal also may have a non-bridging "terminal" oxygen atom. Based on the oxidation state of the heteroatoms and M metal atoms, a heteropolyacid cage structure will bear a negative charge (a "polyoxoanion") that is balanced with a charge-balancing number of suitable cations, including protons. Commonly-used cations include alkali metal ions and ammonium. A "heteropolyacid" ("HPA") contains protons as the charge-balancing ion, while a "polyoxometallate" ("POM") uses at least one non-proton as a charge-balancing ion.

The most typical heteroatom, X, used in heteropolyacids and polyoxometallates is phosphorus, although some or all of X atoms may be selected from suitable Groups 12–16 elements (new IUPAC nomenclature), such as silicon, boron, and antimony. Phosphorus is the preferable X heteroatom used in this invention.

Framework M metals are selected from transition metals and are typically selected from Groups 5 and 6 elements such as molybdenum, vanadium, tungsten, niobium and tantalum. Molybdenum, vanadium, and tungsten and combinations thereof are used most typically. Molybdenum or a combination of molybdenum and vanadium are preferable. Pope et al. propose that suitable metals have an appropriate cation radius and be good oxygen p-π-electron acceptors. Also molybdenum and tungsten may expand their cation valance from four to six that apparently permit these metals to form stable heteropolyacids and polyoxometallates. A mixture of M metals may be used in a heteropolyacid or polyoxometallate, although a major portion of Mo atoms is preferred. A common POM contains molybdenum and vanadium in which the atomic ratio of Mo:V is 5:1 to 17:1, and typically is 11:1. Other preferable POM's contain only molybdenum as the M metal.

Other elements capable of being inserted into the polyoxoanion cage in minor amounts (typically as substitutes for the M metal) including Groups 3–12 elements are designated as "Q" atoms. Examples of such Q atoms include zinc, titanium, zirconium, iron, cobalt, and palladium.

Pope et al. indicate heteropolyacids and polyoxometallates may exist in several structures that relate to specific compositions, coordinations and atomic radii of the M and X metals. A common structure containing one central phosphorus X heteroatom is described as a "Keggin" structure with the associated polyoxoanion referred to as a "Keggin" ion. A commonly-known Wells-Dawson structure typically contains two phosphorus atoms. The typical structure used in the catalyst materials of this invention is the Keggin structure. Structures containing two unshared oxygens, such as the Strandberg structure, are not preferred.

A general composition formula of polyoxoanions useful in this invention is:

$$\{X_xM_mQ_qO_y\}^{-e}$$

wherein X, M, Q, and O are defined above.

The anionic charge (e) of the polyoxoanion cage (represented as the composition between the brackets) is determined by the oxidation states of the atoms within the cage. Typically, x=1–5; m=5–20; q=0–10; and y=18–62.

When such a polyoxoanion is combined with a cation selected according to this invention, a general composition formula of a polyoxometallate useful in this invention is:

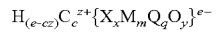
$$H_{(e-cz)}C_c^{z+}\{X_xM_mQ_qO_y\}^{e-}$$

wherein X, M, Q, and O are defined above, H is hydrogen, C is selected from Groups 3–15 and lanthanide metal cations, and preferably is niobium; c is the number of cations C; and z is the charge of cation C. In addition to niobium, C also preferably may be titanium, zirconium, vanadium, yttrium, cerium or chromium.

The anionic charge (e) of the polyoxoanion cage (represented as the composition between the brackets) is determined by the oxidation states of the atoms within the cage. Typically, x=1–5; m=5–20; q=0–10; y=18–62; and c=1–6 for a specific polyoxometallate.

Typical nominal stoichiometric formulae representing Keggin polyoxoanions useful in this invention include:

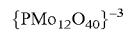
$$\{PMo_{12}O_{40}\}^{-3}$$

$$\{PMo_{11}VO_{40}\}^{-4}$$

$$\{PMo_{10}V_2O_{40}\}^{-5}$$

Typical nominal stoichiometric formulae representing Wells-Dawson polyoxoanions useful in this invention include:

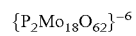
$$\{P_2Mo_{18}O_{62}\}^{-6}$$

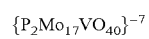
$$\{P_2Mo_{17}VO_{40}\}^{-7}$$

According to this invention, a suitable polyoxometallate is formed and is activated by heating to an activation-effective temperature in the presence of a suitable activation agent. After activation, the activated catalytic material should have significantly higher activity when measured in an oxidation reaction than the corresponding non-activated material. Preferably, activity for an activated catalyst is at least doubled and may be increased by at least one or two orders of magnitude or more. Preferably, such activation agent is a reducing agent that acts during the heating period to partially reduce M metal in the polyoxometallate. Although not bound to a theory of activation, evidence suggests that for a polyoxomolybdate, a pyridine adduct product is a mixed phase material in which after activation contains at least some reduced M metal (e.g. molybdenum) species and some reduced cation (e.g., niobium) species. The active phase is distinct from the pre-activation crystalline phase and does not contain significant amounts (i.e., amounts that affect catalytic activity) of a singular cubic phase that appears when heated to excess temperatures.

In order to form a catalyst precursor useful in this invention, a polyoxometallate typically is combined with a suitable activation species such as pyridinium. A general composition formula for a polyoxometallate in which A is pyridinium and b is the number of pyridinium cations is:

$$H_{(e-(b+cz))}A_b C_c^{z+}\{X_x M_m Q_q O_y\}^{e-}$$

wherein x=1–5; m=5–20; q=0–10; b=1–5; and y=40–62, and b and c are such to balance the charge of the polyoxoanion; b is the number of pyridinium cations; c ($\geq$0.01) is the number of cations C; and z is the charge of cation C.

A typical composition formula of a polyoxometallate precursor, which contains pyridinium (pyr) component useful in this invention, is:

$$H_a(pyr)_b Nb_c\{P_x Mo_m V_n O_y\}$$

wherein x=1 or 2; m=10–18.; n=0–4, b=1–4, c=0.01–2, and y=40–62, and pyridinium is added to balance the charge of the polyoxoanion. If an excess of pyridine is used, a=0. Preferable individual precursor (prior to activation) nominal compositions useful in this invention include:

$(pyr)_{3.0-4}Nb_{0.1-0.25}\{PMo_{12}O_{40}\}$;

$(pyr)_{3.0-4}Nb_{0.1-0.25}\{PMo_{11}VO_{40}\}$;

$(pyr)_{3.0-4}Nb_{0.1-1.0}\{P_2Mo_{18}O_{62}\}$;

$(pyr)_{3.0-4}Nb_{0.1-1.0}\{P_2Mo_{17}VO_{62}\}$;

Mixtures of materials with differing compositions and oxidation states may be present. Although for convenience compositional formulae have proportions of elements represented by integers, analytical measurements indicate fractional amounts that may not correspond to stoichiometry of one structure. Determination of structure (such as Keggin or Wells-Dawson) may be difficult from compositional analysis alone. Thus, a material represented by a stoichiometric formula with integral numbers should be taken as an approximation of an analytical measurement.

An elemental analysis of a polyoxoanion with a nominal formula of $NbPMo_{11}V(pyr)$ indicated a composition formula represented as $(Pyr)_{3.75}Nb_{0.08}\{PMo_{11.15}V_{0.78}O_{40}\}$. Other measured elemental analysis indicated compositions of $(Pyr)_{3.65}Nb_{0.66}\{PMo_{13.27}V_{0.55}O_{40}\}$, with 1.63 wt. % occluded pyridine, and $(Pyr)_{3.65}Nb_{0.26}\{PMo_{11.857}V_{0.74}O_{40}\}$, with 0.53 wt. % occluded pyridine. The elemental analysis approximates a Keggin structure in both cases. It is believed that crystal packing directs about 3.7 molecules of pyridine per HPA anion. The ratio of pyridinium/HPA is dictated by the amount of cation (e.g., Nb).

A composition formula for a preferable niobium polyoxomolybdate catalyst precursor useful in this invention is:

$$(Pyr)_b Nb_c\{PMo_m V_n O_y\}$$

wherein m=10–15; n=0–1, b=3–4, c=0.05–1, and y=35–45.

Polyoxoanions are prepared by techniques known to the art. In a typical procedure, polyoxoanions are prepared by an ether extraction method starting from suitable amounts of molybdate and phosphate at low pH (typically<1). Regulation of the pH may determine the structure of the polyoxoanions. In such a preparation, a source for a M metal, such as a molybdate, a source for a Q metal such as vanadate, a source for the X-element, such as phosphate, are combined with a mineral acid, such as sulfuric acid, to form an acidified mixture. In an ether extraction, diethyl ether is added to the resulting product, which forms an HPA-ether complex from which an acid form of the polyoxoanion can be recovered.

A polyoxometallate is formed by exchanging the polyoxoanion (POA) with suitable cation species. The cationic species may be in the form of a salt such as halides, oxides, hydroxides, nitrates, and oxalates. Oxalate salts, such as niobium oxalate, have been found to be effective for preparing polyoxometallates of this invention. In a typical procedure, an amount of metal cation species is exchanged with the polyoxoanion in water such that about 0.05 to 1 cation species are exchanged per polyoxoanion. Typically less than a stoichiometric amount of metal cation is exchanged onto the polyoxoanion such that about 0.1 to 0.5, preferably to about 0.3, metal cations/POA are exchanged. Usually about 0.25 metal cations are exchanged per POA. For a typical Keggin ion structure, these ratios are reflected in the metal cation/P ratio. In a typical procedure in which an amine is added to the polyoxoanion to form a catalyst precursor, an excess of amine (e.g., pyridine) is added to completely charge balance the anion.

In order to produce the catalytically active materials useful in this invention, a suitable POM is activated to transform the POM starting precursor material into an active catalytic phase. This catalytic phase is a partially reduced POM that typically has been prepared by reduction of a POM precursor under suitable conditions of temperature and atmosphere.

Typical activation conditions include heating a polyoxomolybdate-based starting material in the presence of a suitable reducing agent to an activation temperature for sufficient time to permit partial reduction in a non-oxidizing atmosphere.

Polyoxomolybdate-based catalysts used in this invention are prepared by partially reducing a POM above the activation temperature, but below the temperature at which substantial amounts of catalytically inactive molybdenum oxide ($MoO_3$) are formed. Typical activation temperatures are above about 400° C. and preferably above about 410° C. The activation temperature should be below the temperature at which molybdenum oxide is formed. Typically, $MoO_3$ is formed at about 450° C. Some pyridinium POM's may be heated up to about 560° C. without substantial formation of $MoO_3$. In the presence of pyridine, the POM typically will form $Mo_x$ where x is less than 3 (usually, $MoO_2$, but also $Mo_4O_{11}$, etc). Preferable activation temperatures are about 410 to about 440° C., and most preferably about 415 to 430° C. A typically-used activation temperature is about 420° C. Analysis of a starting material such as $NbPMo_{11}V(pyr)$ by thermogravametric analysis (TGA), in which a sample of material is heated slowly while measuring loss of sample mass, shows loss of pyridine at about 375–425° C. The active catalyst phase, which typically is obtained after a heat treatment at about 400–450° C., may reflect a reduced molybdenum oxide that shows a blue color in the post activation and reaction material.

After heat activation to about 420° C., a pyridinium-containing catalyst precursor contains virtually no pyridine. Typically, both pyridinium ions and occluded pyridine desorb at temperatures below the activation temperature.

Activation by heating to the activation temperature is conducted for a time sufficient for the polyoxomolybdate-based starting material to become partially reduced. Typically, the polyoxomolybdate-based material is heated slowly for up to 12 hours or more.

Preferably, the activation occurs in a non-oxidizing atmosphere, such as a gaseous hydrocarbon, nitrogen, argon, or helium. Oxygen content of the atmosphere should be kept below a level that would interfere with the activation process. Preferably, the atmosphere is substantially free of oxygen. Experiments have demonstrated that activation in air produces catalytically inactive $MoO_3$.

A suitable reducing agent used in the activation should be effective at the activation temperatures. Since the typical activation temperatures may range from 400 to 450° C., a suitable reducing agent must be an effective reducing agent at those temperatures. Although not bound by theory, it is believed that for pyridinium, the organic component decomposes at about the activation temperature and that decomposition products of the pyridinium act as the reducing species at the molecular level. Thus, a material that decomposes significantly below or above the activation temperature would not be preferred as a reducing agent. For the purposes of this invention, the term "reducing agent" includes a material that produces reducing species during the activation process. Examples of suitable reducing agents are organic amines and quaternary ammonium adducts especially aromatic ammonium species. Amines include pyridine and quinoline. Quaternary ammonium adducts include ammonium, tetraalkylammonium, pyridinium, quinoliuum, protonated aromatic and aliphatic amine, and combinations thereof. The preferable adduct is pyridinium. Other suitable reducing agents include carbon monoxide. The preferable reducing agent is pyridine that has been permitted to combine with the polyoxometallate prior to activation in excess of the charge balancing amount.

After activation, the polyoxomolybdate catalytic material of this invention becomes more complex and loses the well-defined structure typical of the starting material as observed by a broadening of x-ray diffraction lines. Additional heating produces a singular cubic phase that is the same phase as observed in a polyoxomolybdate without pyridine. Also, $^{31}P$ NMR indicates that after pretreatment, a Keggin or Wells-Dawson unit is at least partially decomposed. Although there may be a mixture of oxidation states in the catalytic phase, this catalytic phase is not primarily molybdenum oxide ($MoO_3$), which has been determined to be catalytically inactive.

Typically, an activated catalyst phase of this invention is characterized by XRD by broad x-ray diffraction lines (except for low angle lines around $2\theta=9°$) and absence of catalytic inactive phases that form after heating to excess temperature, such as $MoO_3$.

Niobium K edge electronic spectra (XANES) for niobium (IV) oxide (NbO2) and niobium (V) oxide ($Nb_2O_5$) show the near edge shape changes as a function of oxidation state (Nb4+/Nb5+). This allows observation of discernable changes in the average oxidation state of niobium. At room temperature and 200° C., the edge shape is characteristic of niobium in a +5 oxidation state. A shoulder approximately 15 eV above the edge becomes more evident as the temperature is increased to 420° C. causing the spectrum to resemble that of $NbO_2$ (niobium in a 4+ oxidation state).

Molybdenum K edge XANES for $NbPMo_{11}Vpyr$ ($Mo^{6+}$) and molybdenum (II) oxide ($Mo^{4+}$) show subtle changes in the shape of the near edge spectra and offer information regarding the average oxidation state of molybdenum in the sample. XANES was measured for $NbPMo_{11}Vpyr$ during activation to 420° C. and under reaction conditions while observing closely the molybdenum edge. Changes in the near edge features are observed around the shoulder at approximately 20 and 30 eV above the edge over this temperature range and under reaction conditions; these changes suggest a change in the overall oxidation state of the molybdenum species in the catalyst.

Catalyst materials of this invention may be used directly or combined with other materials known in the art such as silicon carbide as diluents. Also, the catalysts may be supported upon suitable inert materials such as refractory oxides, carbides, or other POM's.

The polyoxoanions of the materials of this invention are charge balanced with at least one suitable cation of a Group 3–15 or lanthanide metal. Preferable cations are selected from Group 3–6 metal cations. Preferable cations are niobium, chromium, zirconium, molybdenum, and titanium and the most preferable cation is niobium. Other cations include cations of tantalum, iron, bismuth, copper, tellurium, antimony, cobalt and nickel. Of the cations tested in this invention, niobium, titanium and zirconium polyoxometallates demonstrate a substantial increase in catalytic activity over polyoxometallates containing other cation species, and niobium polyoxometallates show the most substantial increase in catalytic activity. Since the cation undergoes some reduction during the activation process, the cation should not be in its lowest oxidation state, but should be capable of partial reduction under the activation conditions. The preferable cation is the niobium (V) cation.

In a typical procedure, exchange of the heteropolyacid is carried out in aqueous solution in the presence of less than stoichiometric amount of a soluble metal salt, such as a halide or oxalate. For niobium the preferable salt is niobium oxalate. Formation of the pyridinium adduct is achieved by exchange of the niobium polyoxometallate in an excess of pyridine in aqueous solution. A greater than a stoichiometric amount of pyridine may be used such that excess (non-charge balancing) pyridine is present in the material.

Catalysts of this invention typically are dried and formed into shapes and sizes that are appropriate for the oxidation process used according to techniques known in the art. Catalytic material also may be supported upon or diluted with inert material such as silicon carbide, silica, alumina, or silica-alumina.

Desorption of pyridinium species over the temperature range 380 to 420° C. (preferable catalyst activation temperature) from $NbPMo_{12}pyr$ and $NbPMo_{11}Vpyr$ type polyoxometallates is accompanied by significant structural and electronic changes in the catalyst. During this activation period, $^{31}P$ NMR results suggested that the heteropolyanion is transformed into several distinct structural types of molybdates including $PMo_9O_{31}^{6-}$, $PMo_{11}O_{39}^{7-}$ and $(MoO_2)_2 P_2O_7$. Partial decomposition of the Keggin unit in this way results in the formation of mobile molybdenum-oxygen and niobium-oxygen fragments (oxoanions) that likely migrate and combine to form small mixed metal oxide clusters. Due to the irregular shape and size of these clusters, and the irregular structure of the decomposed primary structure, no short range order is observed by in situ X-ray powder diffraction although a repeating unit of approximately 10 Å was observed. After activation of both $NbPMo_{11}Vpyr$ and $(VO)PMo_{11}Nbpyr$, structures with similar Nb—O—Mo coordination numbers and identical interatomic distances are obtained and demonstrate the indifference of the active structure to initial niobium positioning. XPS (X-ray photoelectron spectroscopy) and XANES (K edge electronic spectroscopy) analysis reveal that the charged pyridinium species reduce the molybdenum and niobium centers upon removal from the solid during activation. Reduction of $Nb^{5+}$ to $Nb^{4+}$ was observed by XANES, whereas some non-reduced molybdenum remained in the catalyst after activation with $Mo^{5+}/Mo^{6+}$ ranging from 0.58 at the surface (XPS) to 0.17 in the bulk (XANES).

Materials prepared according to this invention may be used in catalytic conversion processes. These include oxidation, particularly partial oxidation, of hydrocarbons in the presence of a source of oxygen. In such processes, $C_2$ to $C_{20}$ hydrocarbons may be oxidized to oxygen-containing compounds such as alcohols, aldehydes, ketones, furans, carboxylic acids, and anhydrides with selectivity to one or more oxidized products. Specifically, propane may be oxidized to acetic acid, acrylic acid and maleic acid.

Effective catalytic conversion conditions should be chosen by a person skilled in the art such that the conversion proceeds in an efficient manner. A typical conversion temperature is above 100° C. and usually is above about 200° C. and may range up to about 450° C. or above. For hydrocarbon oxidation conversions, preferable temperatures may range from about 250° C. up to about 450° C. and more preferably are about 275° C. to about 375° C. Temperature conditions should be chosen such that the reaction activity is practical while avoiding temperatures at which the catalyst, feedstock, or products decompose or otherwise are adversely affected. An advantage of the catalyst system of this invention is that the catalyst activity is maintained at lower temperatures than with conventional mixed metal catalysts in comparable oxidation processes. At higher temperatures, more selectivity is maintained, together with an increase in activity, in comparison to conventional catalyst systems.

Useful pressures may range from atmospheric to 100 bars or above. Typical reaction pressures are about 1 to 20 bars or more.

Reactor systems known to the art may be used such as fixed bed and fluidized bed systems. Effective reaction contact times may be chosen by a person skilled in the art for the specific system employed and typically range from about 0.001 to about 5 seconds, and preferably are about 0.001 to about 1 second.

A typical feedstock useful in this invention typically contains a reactive material such as a hydrocarbon and a source of an oxidizing material such as oxygen or air, and may contain a diluent such as nitrogen, helium, argon, or another inert fluid and water. The feedstock also may contain other reactive components or combinations of components. Typical reactive materials useful in this invention include hydrocarbons and substituted hydrocarbons containing 2 to about 20 carbon atoms.

Suitable hydrocarbons include alkanes, alkenes, cycloalkanes, cycloalkenes, alkylaromatics, arylalkanes and aryl alkenes. For the purpose of this invention, hydrocarbons also include carbon-containing acyclic and cyclic compounds that also contain one or more heteroatoms such as oxygen, phosphorus, sulfur, and nitrogen. These hydrocarbons also may be substituted with one or more substituents that are compatible with the reactive system used in this invention. Possible substituents include halides, nitrogen-containing substituents such as amines and nitrates, sulfur-containing substituents, phosphorus-containing substituents and oxygen-containing substituents such as aldehydes, alcohols and ketones. Specific examples include ethane, propane, n-butane, isobutane, n-pentane, 2-methylbutane, isopentane, hexane, heptane, octane, ethylene, propylene, 1-butene, 2-butene, isobutene, pentene, isopentene, 1,5-hexadiene, toluene, o-, m-, and p-xylene, cyclohexane, cyclopentane, cyclopentene, cyclohexene, furan, and the like including compounds containing compatible substituents. Preferable reactive hydrocarbons include $C_2$ to $C_6$ alkanes and alkenes and particularly ethane, ethylene, propane, propylene, n-butane, 1-butene, and 2-butene. $C_3$ and linear $C_4$ alkanes and alkenes are most preferred.

In a preferred process, a lower ($C_2$–$C_6$) alkane or alkene is converted by oxidation using a catalyst of this invention. In such conversions, a feedstock preferably containing the alkane, alkene, or mixture thereof together with a source of oxygen, an inert diluent gas such as nitrogen, and typically water is contacted with the catalyst material under conversion conditions. Typical conditions include a reaction temperature of 250 to 425° C., preferably 300 to 400° C., a reaction pressure of 1–20 bar, and a contact time of about 0.001 to 1 second.

Preferable catalyst systems useful in these processes are the activated, partially reduced niobium-exchanged polyoxomolybdates described in this invention. Especially preferred are niobium-exchanged polyoxomolybdates which have been formed from a pyridine adduct that has been heat treated at 375 to 450° C. in a non-oxidizing atmosphere for a period such that a partially reduced, catalytically-active phase is produced.

In another aspect of this invention, hydrocarbons such as $C_3$ and $C_4$ hydrocarbons may be partially oxidized using the catalysts of this invention. In such processes, hydrocarbons such as propane, propylene, and n-butane are passed over catalysts prepared according to this invention under partial oxidation conditions. Typically, the hydrocarbon feed is passed over or through solid catalysts at temperatures above about 250° C. and ranging to 425° C. or above in a suitable reactor system. Optimum reaction conditions, such as temperature and pressure, may be selected through routine experimentation.

In another aspect of this invention, maleic acid (which may be converted to maleic anhydride by removal of water) is formed from both $C_3$ and $C_4$ hydrocarbons. While not bound by theory, dimerization of propylene may produce 1,5-hexadiene and 4-methyl-1-pentene that is oxidized to maleic acid under the chosen reaction conditions. Since maleic anhydride is a commercial product typically formed from butanes using a VPO catalyst, the present invention provides an alternative feedstock and combined with a superior combination of activity and selectivity.

For propane oxidation a catalyst formed from a $\{PMo_{11}VO_{40}\}^{4-}$ precursor polyoxoanion is preferred. For butane oxidation, a catalyst formed from a $\{PMo_{12}O_{40}\}^{3-}$ or $\{PMo_{11}VO_{40}\}^{4-}$ precursor polyoxoanion is preferred.

The following examples illustrate but do not limit the invention described herein.

Experimental

Experiments were performed to use a series of materials as catalysts for propane, propylene, and butane oxidation. In these experiments about 0.2 gram of dried catalyst or catalyst precursor material (prepared as described below), pelletized using a hydraulic press, ground and sieved to 35–60 mesh, was combined with particulate silicon carbide to form about one milliliter total volume. This mixture was placed in a tube reactor through which was passed which a feed of hydrocarbon, oxygen, helium and water (as steam). Gaseous products were directly injected into a GC/MS, while liquid products were trapped in water and later injected by syringe into the GC/MS for product identification and analysis. Catalyst precursors were activated in situ to form catalytic material by passing a stream of oxygen-free helium through the material during the activation (heating) process.

Typically, reactivity experiments were performed in a BTRS Jr. reactor (Autoclave Engineers) with a stainless steel reactor tube. Two tenths gram (0.2 g) catalyst (35–60 mesh) was mixed with 1 mL SiC (16 mesh, Abrasives Unlimited) and held in the reactor with glass wool. Reactant flow was single pass. The catalyst sample was pretreated by heating to 420° C. over 5 hours and then held for 6 hours at that temperature before cooling to 380° C. in flowing He. Feed gasses included n-butane (99.9%, Matheson), oxygen (99.5%, Air Liquide), and 5% Ar/He (99.999%, Air Liquide). Standard flow rates were 4:2:4:5 mL/min of n-butane:oxygen:helium/argon:steam. Water was injected to the reactor feed flow via a syringe pump to form steam. Total pressure in the reactor was atmospheric. Standard reaction temperature was 380° C.

Feed to the reactor was initiated and allowed to equilibrate for one hour, at which point sampling was initiated. Reported data are the average values for the second hour on stream. Reactant and product analyses were by GCMS using a HP GCD Plus with a HP-Plot Q column. Gas analysis was performed online while oxygenated products were trapped in an ice bath and analyzed offline. Experiments using ethane (99.99%, Matheson), propane (99.98%, Matheson) and isobutane (99%, Matheson) were performed similarly. For the toluene experiment, the helium/oxygen reactant was fed through a bubbler containing toluene (99.8%, Aldrich) at room temperature.

Surface area measurements (BET) were performed on a Coulter Omnisorp 100 using nitrogen (99.996%, Air Liquide) adsorption at 77K. Surface areas were determined after pretreating to 420° C.

Elemental analysis was performed by Galbraith Laboratories Inc., Knoxville, Tenn.

Preparation of catalyst and catalyst precursors are described below. For convenience, a nominal composition formula is provided. However, actual elemental analysis typically yields fractional amounts. Also, for convenience, the material is identified as containing the C, M, X, and Q elements. The amount of oxygen or hydrogen in the composition will follow valence rules.

Catalysts and catalyst precursors were prepared as follows:

11-Molybdo-1-vandanophosphoric acid—$H_4\{PMo_{11}VO_{40}\}$ "$PMo_{11}V$"

Fifty millimoles (6.1 grams) of sodium metavanadate ($NaVO_4$) were dissolved in 100 milliliters: of distilled water heated to 80° C. with stirring for 60 minutes. After cooling to room temperature, this solution was combined with a solution of sodium hydrogen phosphate ($Na_2HPO_4$; 7.1 grams; 50 mmol) that had been prepared in 100 milliliters of distilled water at room temperature with stirring. After the combined solution was acidified with 5 milliliters of concentrated sulfuric acid, the solution became dark red in color. This solution was combined with a solution of sodium molybdate dihydrate ($Na_2MoO_4.2H_2O$: 133.0 grams; 550 mmol) that had been prepared in 200 milliliters of distilled water with stirring at room temperature. Concentrated sulfuric acid (85 milliliters) was added very slowly over 90 minutes to the combined solutions with vigorous stirring. This addition was exothermic and resulted in a clear bright red solution. Diethyl ether (200 milliliters) was added to the aqueous solution (300 milliliters) in a separating funnel. After shaking, three layers formed in the funnel—a top yellow ether layer, an aqueous orange central layer, and a thick dark red bottom layer, which was a HPA-etherate complex. The remaining portion of the acidified solution was extracted according to this procedure and the HPA-etherate layers were combined. Ether was removed from the HPA layer by bubbling air through the layer over night. The resulting thick red syrup was dissolved in water and recrystallized. Red/orange crystals of 11-molybdo-1-vandanophosphoric acid were dried overnight at 100° C. (yield: 43.08 grams).

$NbH\{PMo_{11}VO_{40}\}$ "$NbMo_{11}V$"

Niobium pentachloride ($NbCl_5$; 1.21 grams; 4.48 mmol) was dissolved in 10 milliliters of water and basified with 1 milliliter of aqueous ammonium hydroxide to precipitate a white solid, which was recovered by filtration. The solid was dissolved in a 20-milliliter aqueous solution of oxalic acid (1.01 grams; 11.2 mmol). The resulting niobium oxalate solution was added slowly to a solution of 20 grams of $H_4\{PMo_{11}VO_{40}\}$ in 40 milliliters of water. The combined solutions were stirred and heated to 80° C. until the liquid had evaporated to leave an olive green solid (yield 19.52 grams of $NbH(PMo_{11}VO_{40})$).

$NbH\{PMo_{11}VO_{40}\}(Pyr)$ "$NbPMo_{11}V(pyr)$"

An aqueous pyridine solution (1.65 grams (21 mmol) in 10 milliliters of water) was added dropwise to an aqueous slurry of 5.26 grams of $NbH(PMo_{11}VO_{40})$ in 30 milliliters of water. The mixture was dried in air at 70–80° C., pelletized using a press, and ground and sieved to 35–60 mesh.

$PMo_{11}VO_{40}(pyr)$ "$PMo_{11}V(pyr)$"

The procedure described in the preparation of $NbPMo_{11}V$ (pyr) was followed substituting $H_4\{PMo_{11}VO_{40}\}$ for $NbH\{PMo_{11}VO_{40}\}$.

$PMo_{11}Nb(pyr)$

Phosphomolybdic acid (5.00 g) was dissolved in water (27.4 mL). The pH of the solution was then adjusted to 4.4 using lithium carbonate $Li_2CO_3$ (0.583 g) to form a lacunary Keggin ion structure. Niobium oxalate was then prepared as above and added to the solution. The solution was then stirred for 2 hours to form $PMo_{11}NbO_{40}$. Pyridine was then added (0.216 g) and a yellow precipitate was formed, filtered off, and dried.

$NbPMo_{12}(pyr)$

Niobium pentachloride (1.210 g) was dissolved in water (10 mL) and the solution basified by using ammonium hydroxide (0.5 mL). The white precipitate was removed by filtration and dissolved in oxalic acid (1.008 g in 20 mL water). The niobium oxalate solution was then slowly added to $PMo_{12}$ (20 g) (Aldrich Chemical) dissolved in water (40 mL). The mixture was stirred and heated to 80° C. until the liquid had evaporated. An aqueous solution of pyridine (1.645 g in 10 mL water) was slowly added to a slurry of the niobium polyoxometalate ($NbPMo_{12}$) (5.260 g) in water (30 mL) to form an immediate precipitate. The mixture was stirred and evaporated to dryness at 80° C.

For $MoPMo_{12}pyr$, ammonium molybdate $(NH_4)_2MoO_4$ (0.082 g) was dissolved in water with Dowex 50x8-200 proton form ion exchange resin (0.17 g) and stirred for 1.5 hours. The resin was filtered off and oxalic acid (0.073 g) was added. The molybdenum oxalate solution was then added to phosphomolybdic acid (1.5 g) and pyridine exchanged as above. For $ZrPMo_{12}pyr$, zirconium sulfate $Zr(SO_4)_2$ (0.292 g) was dissolved in water (20 mL) and basified with ammonium hydroxide. The white precipitate was removed by filtration and dissolved in oxalic acid (0.187 g in 20 mL water). The zirconium oxalate solution was then slowly added to $PMo_{12}$ (1.5 g) dissolved in water (40 mL), and evaporated and pyridine exchanged as above. For $TiPMo_{12}pyr$, titanium oxalate $Ti(C_2O_4)$ (0.064 g) was dis solved in water (20 mL). The titanium oxalate was then added to added to $PMo_{12}$ (0.75 g) dissolved in water (40 mL) and pyridine exchanged. For $VPMo_{12}$pyr, vanadium pentoxide $V_2O_5$ (0.046 g) was dissolved in water (40 mL) and then added to oxalic acid in water (0.136 g in 10 mL). This solution then was added to $PMo_{12}$ (1.5 g), dissolved in water (40 mL) and pyridine exchanged. For $CrPMo_{12}$pyr, chromium trioxide $CrO_3$ (0.051 g) was dissolved in water (10 mL) and then added to oxalic acid in water (0.182 g in 10 mL). This solution was then added to $PMo_{12}$ (1.5 g) dissolved in water (40 mL) and pyridine exchanged.

$NbP_2Mo_{18}$(pyr)

Sodium monohydrogen phosphate $Na_2HPO_4.12H_2O$ (7.14 g) was dissolved in a mixture of perchloric acid (75 mL) and water (50 mL). The solution was cooled to 20° C. Then a solution of sodium molybdate $Na_2MoO_4.2H_2O$ (108.27 g) in water (200 mL) was added dropwise to the above solution. The resulting solution was clear yellow. The solution was allowed to evaporate in air and after two weeks yellow crystals of $Na_6P_2Mo_{18}O_{62}$ formed. Formation of the Wells-Dawson unit was confirmed by single crystal diffraction. The crystals were filtered off and proton, niobium, and pyridine exchanged as above.

$NbP_2Mo_5$(pyr)

Sodium molybdate $Na_2MoO_4.2H_2O$ (24.682 g) and sodium dihydrogen phosphate $NaH_2PO_4.2H_2O$ (6.369 g) were added to 10.5 mL of perchloric acid. Distilled water was added to increase the total volume to 50 mL and the solution was stirred to aid dissolution. The resulting solution was clear. The solution was allowed to evaporate in air and after two weeks clear crystals of $Na_6P_2Mo_5O_{23}$ formed. Formation of the Strandberg unit was confirmed by single crystal diffraction. The sodium form was then converted to an exchangeable form by dissolving (4.008 g) in 20 mL water and adding Dowex 50x8-200 ion exchange resin (1.567 g) and stirring for 90 min to form $Na_4H_2P_2Mo_5O_{23}$. The resin was filtered off and the sample subsequently niobium and pyridine exchanged as above. Stability of the Strandberg unit throughout the synthesis procedure was confirmed by the presence of a $^{31}P$ NMR peak at approximately 2 ppm.

$NbMo_8$(pyr)

The procedure of Gili et al. was adapted for pyridine. An aqueous solution of pyridine (1.931 g in 120 mL of distilled water) was added to an aqueous suspension of $MoO_3$ (3.213 g of $MoO_3$ in 1800 mL of distilled water). The mixture was heated under reflux with stirring for 6 hours, cooled in an ice bath, and filtered. The solution was then reduced to 600 mL by a rotary evaporator and allowed to stand overnight whereupon a white precipitate formed $(C_5H_5NH)_4(Mo_8O_{26})$. The crystals were filtered, washed with water, and dried. Powder diffraction and TGA curves were identical to those of McCarron et al. The sample was then niobium exchanged as above.

Molydophosphoric acid $H_3\{PMo_{12}O_{40}\}$ "$PMo_{12}$"

Sodium hydrogenphosphate dihydrate $Na_2HPO_4.2H_2O$ (7.14 g) was dissolved in a mixture of perchloric acid (73 ml) and water (20 ml). Then a solution of sodium molybdate $Na_2MoO_4.2H_2O$ (108 g) in water (200 ml) was added dropwise to the above solution at 20° C. The solution was allowed to evaporate in air over several days after which orange crystals of $H_3\{PMo_{12}O_{40}\}$ were obtained. Other preparation procedures are found in Inorg. Chem. (1983) 22, 207 and J. Catal. (1994) 146, 491, incorporated by reference herein.

$NbH\{PMo_{12}O_{40}\}$ "$NbPMo_{12}$"

The procedure described in the preparation of $NbMo_{11}V$ was followed, substituting $H_3\{PMo_{12}O_{40}\}$ for $H_4\{PMo_{11}VO_{40}\}$.

$PMo_{12}O_{40}$(pyr) "$PMo_{12}$(pyr)"

The procedure described in the preparation of $NbPMo_{11}V$ (pyr) was followed substituting $H_3\{PMo_{12}O_{40}\}$ for $NbH\{PMo_{11}VO_{40}\}$.

$NbH\{PMo_{12}O_{40}\}$(pyr) "$NbPMo_{12}$(pyr)"

The procedure described in the preparation of $NbPMo_{11}V$ (pyr) was followed substituting $NbH\{PMo_{12}O_{40}\}$ for $NbH(PMo_{11}VO_{40})$. Phosphomolybdic acid was purchased from Aldrich. Niobium pentachloride (1.210 g) was dissolved in water (10 mL) and the solution basified by using ammonium hydroxide (0.5 mL). The white precipitate was removed by filtration and dissolved in oxalic acid (1.008 g in 20 mL water). The niobium oxalate solution was then slowly added to $PMo_{12}$ (20 g) dissolved in water (40 mL). The mixture was stirred and heated to 80° C. until the liquid had evaporated. An aqueous solution of pyridine (1.645 g in 10 mL water) was slowly added to a slurry of the niobium polyoxometalate ($NbPMo_{12}$) (5.260 g) in water (30 mL) to form an immediate precipitate. The mixture was stirred and evaporated to dryness at 80° C.

$TiH\{PMo_{12}O_{40}\}$(pyr) "$TiPMo_{12}$(pyr)"

Titanium oxalate dehydrate $(Ti(C_2O_4).2H_2O$; 0.064 grams) was dissolved in 10 milliliters of water and added slowly to a solution of 0.75 grams of $H_3\{PMo_{12}O_{40}\}$ in 10 milliliters of water. The combined solutions were stirred and heated to 80° C. until the liquid had evaporated. Water (10 milliliters) was added to the resulting solid with stirring, followed by a solution of pyridine (0.25 milliliters) in water (5 milliliters). The liquid was evaporated with stirring at 80° C.

$YH\{PMo_{12}O_{40}\}$(pyr) "$YPMo_{12}$(pyr)"

Yttirium nitrate hexahydrate $(Y(NO_3)_3.6H_2O$; 0.097 grams) was dissolved in 10 milliliters of water and added slowly to a solution of 0.75 grams of $H_3\{PMo_{12}O_{40}\}$ in 10 milliliters of water. The combined solutions were stirred and heated to 80° C. until the liquid had evaporated. Water (10 milliliters) was added to the resulting solid with stirring, followed by a solution of pyridine (0.25 milliliters) in water (5 milliliters). The liquid was evaporated with stirring at 80° C.

$CeH\{PMo_{12}O_4\}$(pyr) "$CePMo_{12}$(pyr)"

Ammonium cerium nitrate $((NH_4)_2Ce(NO_3)_6$; 0.276 grams) was dissolved in 10 milliliters of water and added slowly to a solution of 1.52 grams of $H_3\{PMo_{12}O_{40}\}$ in 10 milliliters of water. The combined solutions were stirred and heated to 80° C. until the liquid had evaporated. Water (10 milliliters) was added to the resulting solid with stirring, followed by a solution of pyridine (0.5 milliliters) in water (10 milliliters). The liquid was evaporated with stirring at 80° C.

$CrH\{PMo_{12}O_{40}\}$(pyr) "$CrPMo_{12}$(pyr)"

Chromium oxide $(CrO_3$; 0.0506 grams) was dissolved in 10 milliliters of water and added to oxalic acid solution (0.182 g in 10 ml water). The solution was added slowly to a solution of 1.5 grams of $H_3\{PMo_{12}O_{40}\}$ in 10 milliliters of water. The combined solutions were stirred and heated to 80° C. until the liquid had evaporated. Water (10 milliliters) was added to the resulting solid with stirring, followed by a solution of pyridine (0.5 milliliters) in water (10 milliliters). The liquid was evaporated with stirring at 80° C.

VH{PMo$_{12}$O$_{40}$}(pyr) "VPMo$_{12}$(pyr)"

Vanadium oxide (V$_2$O$_5$; 0.1365 grams) was dissolved in 10 milliliters of water and added to oxalic acid solution (0.1365 g in 10 ml water). The solution was added slowly to a solution of 1.5 grams of H$_3${PMo$_{12}$O$_{40}$} in 10 milliliters of water. The combined solutions were stirred and heated to 80° C. until the liquid had evaporated. Water (10 milliliters) was added to the resulting solid with stirring, followed by a solution of pyridine (0.5 milliliters) in water (10 milliliters). The liquid was evaporated with stirring at 80° C.

ZrH{PMo$_{12}$O$_{40}$}(pyr) "ZrPMo$_{12}$(pyr)"

Zirconium sulfate tetrahydrate (Zr(SO$_4$)$_2$.4H$_2$O; 0.1796 grams) was dissolved in 10 milliliters of water and 1 milliliter of aqueous ammonium hydroxide added to the solution to precipitate a solid, which was recovered by filtration. The solid was dissolved in a 10-milliliter aqueous solution of oxalic acid (0.1138 grams). The resulting solution was added slowly to a solution of 1.5 grams of H$_3${PMo$_{12}$O$_{40}$} in 10 milliliters of water. The combined solutions were stirred and heated to 80° C. until the liquid had evaporated. The solid was rehydrated (10 milliliters of water) and an aqueous pyridine solution (0.5 grams in 10 milliliters of water) was added dropwise to the mixture with stirring. The liquid was evaporated with stirring at 80° C.

Literature Preparations

The following materials were prepared according to the cited literature references, all incorporated by reference herein.

BiP Mo$_{12}$O$_{40}$ Ai, M., 8$^{th}$ International Congress on Catalysis, Berlin, *DECHEMA*, 1984, 5, 475.

H$_5$P Mo$_{12}$V$_2$O$_{40}$ Centi, G., Lena, V., Trifiro, F., Ghossoub, D., Aissi, C. F., Guelton, M., Bonnelle, J. P., *J. Chem. Soc. Faraday Trans.*, 1990, 86, 2775.

MoSbVNbO$_x$ M. Takahashi, X. Tu, T. Hirose, M. Ishii (Toagosei Co., Ltd.), U.S. Pat. No. 6,060,422, 2000.

MoVNbTeO$_x$ T. Ushikubo, H. Nakamura, Y. Koyasu, S. Wajiki (Mitsubishi Kasei), U.S. Pat. No. 5,380,933, 1995.

CsFe(PMo$_{11}$VO$_{40}$) (N. Mizuno, D. Suh, W. Han, T. Kudo, Appl. Catal. A, 1996, 114, 309.)

EXAMPLES AND COMPARATIVE RUNS

Examples 1–4

Comparative Runs A–C

A series of experiments was performed in which propane was oxidized using varying catalyst materials. In these experiments, a hydrocarbon (propane) rich, oxygen-containing gas stream was passed through a tube containing catalyst material at 380° C. at a space velocity of 9,000 l/l/h (corresponding to a residence time in the reactor tube of 0.42 seconds). The reactant ratios were C$_3$/O$_2$/He/H$_2$O=4/2/4/5. Products were determined by GC/MS.

For activation of the catalyst precursor, solid catalyst precursor (pelletized, ground and sieved to 35–60 mesh) was placed in a reactor tube and heated from room temperature to 420° C. at 1.33° C./min under flowing helium at 30 ml/min and maintained at 420° C. for six hours. The temperature was decreased over one hour to the temperature at which the oxidation reaction is carried out.

Each catalyst material was prepared as described above and each had been processed through the activation procedure also as described above before oxidation of propane. The results are shown in Table 1.

TABLE 1

| Ex./Run | Catalyst or precursor | Conversion (%) C$_3$ | O$_2$ | Selectivity (%) CO$_x$ | C$_3^-$ | Ac | AA | MA | Space time yield[2] Ac | AA |
|---|---|---|---|---|---|---|---|---|---|---|
| A | PMo$_{11}$V[3] | 0.4 | 3.4 | 30.2 | 53.9 | 3.5 | 0.0 | — | 3.1 × 10$^{-4}$ | 0 |
| B | NbPMo$_{11}$V[3] | 1.4 | 5.7 | 21.8 | 44.0 | 16.2 | 9.8 | — | 3.4 × 10$^{-3}$ | 1.4 × 10$^{-3}$ |
| C | PMo$_{11}$V(pyr)[1,3] | 3.4 | 10.1 | 10.1 | 36.8 | 30.0 | 17.1 | — | 0.0145 | 5.5 × 10$^{-3}$ |
| 1 | NbPMo$_{12}$ (pyr)[4] | 18 | 95 | 64.8 | 1.0 | 3.3 | 5.5 | 21 | 0.0604 | 0.067 |
| 2 | NbPMo$_{11}$V (pyr)[4] | 21 | 76 | 11 | — | 23 | 49 | 15 | | 0.62 |
| 3 | NbPMo$_{11}$V (pyr)[3] | 25 | 100 | 65 | — | 3 | 3 | 29 | | 0.012 |
| 4 | NbPMo$_{11}$V (pyr)[4] | 8 | 55 | 45 | — | 8 | 17 | 23 | | 0.16 |

C$_3$ = propane;
CO$_x$ = CO + CO$_2$;
C$_2^-$ = ethylene;
C$_3^-$ = propylene;
Ac = acetic acid;
AA = acrylic acid
[1]gas velocity = 36,000 l/l/h; residence time = 0.10 seconds;
[2]STY(mmol min$^{-1}$(g of catalyst)$^{-1}$);
[3]Flow rates: 8:4:8:10 mL min$^{-1}$ (C$_3$/O$_2$/He/H$_2$O);
[4]Flow rates: 32:16:32:40 mL min$^{-1}$ (C$_3$/O$_2$/He/H$_2$O)

Maleic acid (MA) was observed in the liquid product for both NbHPMo$_{12}$O$_{40}$(pyr) and NbHPMo$_{11}$VO$_{40}$(pyr). If MA is included in calculations, the space time yield (STY) for MA was 0.197 (selectivity=21%) and 0.143 mmol min$^{-1}$ (g of catalyst)$^{-1}$ (selectivity=15%), respectively.

Examples 5–6

Another series of experiments was conducted in which propylene was oxidized using NbPMo$_{11}$V(pyr) as the catalyst material precursor at oxidizing conditions as described above, but at 395° C. and varying gas velocities. Results are shown in Table 2.

TABLE 2

| Ex. | GHSV (l/l/h) | Conversion (%) | | Selectivity (%) | | | | | | Space time yield (mmol min$^{-1}$(g of catalyst)$^{-1}$) | |
|---|---|---|---|---|---|---|---|---|---|---|---|
| | | $C_3^=$ | $O_2$ | $CO_x$ | $C_2^=$ | Ac | PA | AA | MA | AA | MA |
| 5 | 9000 | 27 | 100 | 59.4 | 5.3 | 8.4 | 5.5 | 7.8 | 10.1 | 0.0245 | 0.0237 |
| 6 | 36,000 | 29 | 88 | 42.6 | 3.2 | 14.8 | 4.5 | 11.5 | 20.9 | 0.128 | 0.176 |

$CO_x$ = CO + $CO_2$;
$C_2^=$ = ethylene;
$C_3^=$ = propylene;
Ac = acetic acid;
AA = acrylic acid
PA = propionic acid;
MA = maleic acid As observed in Table 2, maleic acid was formed in relatively high yield from propylene with other products including acetic acid, acrylic acid, and propionic acid, together with smaller amounts of propane, propanal, 3-buten-2-one, cyclopentenone, and cyclopentendione isomers, furan, furan derivatives, and pyranones. In a similar experiment using liquid 1,5 hexadiene feed under oxygen lean conditions using a saturated helium carrier, maleic acid was the primary product, followed by acetic acid and other products found in propylene oxidation.

Example 7

In another experiment propane-1-$^{13}$C was used as the feedstock. NMR analysis of the products confirmed that maleic acid originated from the propane.

Examples 8–9

Comparative Run C

Further, samples of molybdovanadophosphoric acid ($PMo_{11}V$) was exchanged with zirconium and vanadium ions, excess pyridine added, and used as a propane oxidation catalyst (after activation) as described above. Also, a conventional VPO catalyst, such as described in U.S. Pat. No. 4,647,673 incorporated by reference therein, was used in a similar propane oxidation experiment. Results are shown in Table 3.

TABLE 3

| Ex/Run | Catalyst | GHSV (l/l/h) | Conversion (%) | | Selectivity (%) | | | | | | Space time yield (mmol min$^{-1}$(g of catalyst)$^{-1}$) | |
|---|---|---|---|---|---|---|---|---|---|---|---|---|
| | | | $C_3$ | $O_2$ | $CO_x$ | $C_2^=$ | $C_3^=$ | Ac | AA | MA | AA | MA |
| C | VPO | 9000 | 2 | 10 | 16.3 | 0 | 42.3 | 15.2 | 12.6 | 12.2 | 3.35 × 10$^{-3}$ | 2.43 × 10$^{-3}$ |
| 8 | Zr | 4500 | 10 | 67 | 60.7 | 3.8 | 2.4 | 9.5 | 11.8 | 11.5 | 8.44 × 10$^{-3}$ | 6.16 × 10$^{-3}$ |
| 9 | V | 4500 | 1.2 | 4 | 9.2 | 3.9 | 67.0 | 12.9 | 6.4 | 0 | 6.5 × 10$^{-4}$ | 0 |

$CO_x$ = CO + $CO_2$;

$C_2^=$ = ethylene;

$C_3^=$ = propylene;

Ac = acetic acid;

AA = acrylic acid

PA = propionic acid;

MA = maleic acid

Zr = $ZrPMo_{11}V(pyr)$;

V = $VPMo_{11}V(pyr)$

Examples 10–12

Another series of experiments was conducted in which propane was oxidized using $NbP_2Mo_{17}V(pyr)$ (Wells-Dawson structure) {in Examples 13–15} and $NbPMo_{11}V(pyr)$ (Keggin structure) {in Examples 10–12} as the catalyst material precursors using activation and reaction conditions as described for Example 1, but at a reaction temperature of 355° C. (except 295° C. for Ex. 12) and varying gas velocities. Results are shown in Table 4.

TABLE 4

| Ex/Run | GHSV (l/l/h) | Conversion (%) | | Selectivity (%)[1] | | | | | | Space time yield (mmol min$^{-1}$(g of catalyst)$^{-1}$) | | |
|---|---|---|---|---|---|---|---|---|---|---|---|---|
| | | $C_3$ | $O_2$ | $CO_x$ | $C_2^=$ | $C_3^=$ | Ac | AA | MA | Ac | AA | MA |
| 10 | 12000[2] | 16 | 100 | 49.7 | 1.2 | 1.0 | 12.4 | 7.0 | 28.3 | 0.071 | 0.027 | 0.081 |
| 11 | 48000[3] | 20 | 96 | 27.8 | 1.6 | 1.4 | 11.9 | 14.2 | 42.5 | 0.303 | 0.241 | 0.542 |
| 12 | 48000[3] | 3 | 28 | 30.5 | 0.7 | 6.4 | 25.2 | 12.6 | 20.1 | 0.079 | 0.026 | 0.031 |
| 13 | 10000[2] | 25 | 99 | 14.9 | 1.3 | 0.3 | 19.0 | 21.1 | 43.0 | 0.241 | 0.178 | 0.272 |
| 14 | 40000[3] | 21 | 76 | 10.7 | 1.6 | 0.5 | 22.8 | 48.5 | 14.9 | 0.487 | 0.691 | 0.159 |
| 15 | 10000[2] | 25 | 94 | 16.0 | 1.8 | 0.2 | 19.6 | 36.2 | 25.4 | 0.164 | 0.203 | 0.107 |

[1]$CO_x = CO + CO_2$; $C_2^=$ = ethylene; $C_3^=$ = propylene; Ac = acetic acid; AA = acrylic acid; PA = propionic acid; MA = maleic acid
[2]$\tau = 0.4$;
[3]$\tau = 0.1$ Examples 16–45

Comparative Runs D–F

A series of oxidations using n-butane as a feedstock was conducted with a selection of material used as a catalyst. A packed tube reactor was used and operated at 380° C. with the feedstock molar ratios of $C_4:O_2:He:H_2O=4:2:4:5$. STY was reported at the highest value at 380° C. and may have been measured at higher flow rates. Table 5 shows n-butane oxidation results using as a selection of materials as catalysts including $MoO_3$, a physical mixture of $MoO_3$, $V_2O_5$, niobium ($Nb_2O_5$) and pyridine, and a conventional VPO catalyst such as described in U.S. Pat. No. 4,647,673, incorporated by reference herein. The octamolybdate was made by refluxing $MoO_3$ and pyridine in water, followed by removal of the water in vacuo and then allowed to stand for overnight. The octamolybdate was subsequently exchanged with niobium using the procedure described in Example 1.

TABLE 5

| Ex/Run | Catalyst | Conversion (%) | | Selectivity (%)[1] | | | | | STY[2] |
|---|---|---|---|---|---|---|---|---|---|
| | | $C_4$ | $O_2$ | CO | $CO_2$ | Ac | AA | MA | |
| D | $MoO_3$ | 0.7 | 20 | 84 | 11 | 2.4 | — | — | 0 |
| E | Physical Mixture | 12 | 95 | 22 | 38 | 18 | 3 | 20 | 0.017 |
| 16 | $NbPMo_{12}$ | 3 | 32 | 7 | 6 | 7 | 2 | 70 | 0.017 |
| 17 | $PMo_{12}(pyr)$ | 13.5 | 89 | 5 | 9 | 3 | 1 | 82 | 0.087 |
| 18 | $PMo_{12}(pyr)^3$ | 7 | 55 | 4 | 6 | 4 | 1 | 83 | 0.054 |
| 19 | $NbPMo_{12}pyr$ | 15* | 100 | 9 | 16 | 3 | 1 | 72 | 0.085 |
| 20 | $NbPMo_{12}pyr^4$ | 15 | 100 | 2 | 3 | 3 | 1 | 90 | 0.85 |
| 21 | $NbPMo_{12}pyr^{3,4}$ | 14 | 91 | 2 | 3 | 4 | 1 | 89 | 0.76 |
| 22 | $PMo_{11}V$ | 0.5 | 9 | 9 | 23 | 17 | — | 50 | $1.6 \times 10^{-3}$ |
| 23 | $NbPMo_{11}V$ | 0.4 | 9 | 31 | 11 | 19 | 4 | 25 | $6.3 \times 10^{-4}$ |
| 24 | $PMo_{11}Vpyr$ | 13.5 | 90 | 2 | 3 | 3 | 1 | 90 | 0.11 |
| 25 | $PMo_{11}Vpyr^3$ | 2 | 29 | 7 | 9 | 4 | 1 | 78 | 0.013 |
| 26 | $NbPMo_{11}Vpyr$ | 15[5] | 100 | 5 | 11 | 5 | 2 | 76 | 0.090 |
| 27 | $NbPMo_{11}Vpyr^4$ | 14 | 95 | 4 | 5 | 5 | 3 | 80 | 0.76 |
| 28 | $NbPMo_{11}Vpyr^{3,4}$ | 13 | 83 | 15 | 12 | 10 | 4 | 59 | 0.56 |
| 29 | $NbPMo_{11}Vpyr^{3,6}$ | 15[5] | 95 | 9 | 15 | 11 | 3 | 62 | 0.14 |
| 30 | $NbPMo_{11}Vpyr^7$ | 9 | 75 | 10 | 16 | 12 | 2 | 60 | 0.033 |
| 31 | $NbMo_8O_{26}pyr$ | 15[5] | 99 | 18 | 32 | 10 | 2 | 37 | 0.16 |
| 32 | $CrPMo_{12}(pyr)$ | 14 | 96 | 14 | 23 | 4 | 3 | 55 | 0.096 |
| 33 | $CrPMo_{12}(pyr)^8$ | 6 | 43 | 5 | 10 | 2 | 2 | 81 | 0.23 |
| 34 | $VPMo_{12}(pyr)$ | 14 | 91 | 14 | 21 | 3 | 3 | 53 | 0.045 |
| 35 | $VPMo_{12}(pyr)^6$ | 7 | 61 | 22[10] | | | | 54 | 0.17 |
| 36 | $MoPMo_{12}(pyr)$ | 7 | 51 | 11[10] | | | | 79 | 0.38 |
| 37 | $NbPMo_{12}(pyr)$ | 15[5] | 100 | 8 | 14 | 3 | 1 | 71 | 0.084 |
| 38 | $NbPMo_{12}(pyr)^4$ | 15 | 100 | 5[10] | | 3 | 1 | 90 | 0.84 |
| 39 | $NbPMo_{12}(pyr)^{11}$ | 9 | 60 | 17[10] | | 12 | 13 | 49 | 0.56 |

TABLE 5-continued

| Ex/Run | Catalyst | Conversion (%) | | Selectivity (%)[1] | | | | | |
|---|---|---|---|---|---|---|---|---|---|
| | | $C_4$ | $O_2$ | CO | $CO_2$ | Ac | AA | MA | STY[2] |
| 40 | $ZrPMo_{12}$(pyr) | 15[5] | 100 | 18 | 28 | 4 | 2 | 47 | 0.056 |
| 41 | $ZrPMo_{12}$(pyr)[9] | 7 | 41 | 4 | 5 | 5 | 2 | 83 | 0.17 |
| 42 | $CePMo_{12}$(pyr) | 11 | 70 | 2 | 4 | 12 | 4 | 78 | 0.065 |
| 43 | $TiPMo_{12}$(pyr) | 15[5] | 100 | 15 | 17 | 5 | 2 | 60 | 0.071 |
| 44 | $TiPMo_{12}$(pyr)[8] | 8 | 60 | 11 | 13 | 4 | 2 | 69 | 0.39 |
| 45 | $YPMo_{12}$(pyr) | 14 | 92 | 7 | 14 | 3 | 2 | 74 | 0.08 |
| F | VPO | 2 | 41 | 14 | 22 | 5 | 2 | 57 | 0.014 |

[1] Ac = acetic acid; AA = acrylic acid; MA = maleic acid;
[2] STY = Space Time Yield (mmol min$^{-1}$(g or catalyst)$^{-1}$) of MA;
[3] Reaction temperature = 340° C.;
[4] Flow rate = 32:16:32:40 (ml/min);
[5] Theoretical maximum conversion; other carbon conversions based on total products formed.
[6] Flow rate = 8:4:8:10;
[7] Reaction temperature = 300° C.;
[8] Flow rate = 27:16:32:40
[9] Flow rate = 16:8:16:20;
[10] $CO_x$;
[11] Flow rate = 64:32:64:80;

Examples 46–51

In another experiment, the relative amounts of niobium and pyridine were varied in a $NbPMo_{12}$(pyr) based catalyst. These catalysts were prepared by ion exchanging the desired amount of Nb and then adding excess pyridine. Therefore, even though one sample was completely exchanged with Nb, pyridine also was present. The reported. Nb/pyr ratio is the theoretical value assuming that all of the Nb oxalate exchanges for protons with pyridine then exchanging for the remaining protons. Oxidation of n-butane was conducted using 0.1 g of catalyst and other conditions as described in Example 1 at a reaction temperature of 380° C. with feedstock mixture ratio of 4:2:4:5. Results are shown in Table 6 for butane oxidation at maximum flow conditions (32:16:32:40) at 380° C.

TABLE 6

| Ex. | Nb/P | Pyr/P | Nb/pyr | Conversion (%) | | Selectivity (%)[1] | | | | | |
|---|---|---|---|---|---|---|---|---|---|---|---|
| | | | | C | O | CO | $CO_2$ | Ac | AA | MA | STY[2] |
| 46 | 0.1 | 6.5 | 0.015 | 4 | 38 | 19 | 15 | 6 | 3 | 55 | 0.17 |
| 47 | 0.25 | 5.75 | 0.04 | 11 | 75 | 17 | 21 | 6 | 4 | 50 | 0.47 |
| 48 | 0.5 | 4.5 | 0.5 | 12 | 82 | 16 | 17 | 5 | 3 | 56 | 0.93 |
| 49 | 1.0 | 2.0 | 0.5 | 10 | 56 | 12 | 12 | 5 | 3 | 68 | 0.66 |
| 50 | 1.17 | 1.17 | 1.0 | 6 | 51 | 13 | 16 | 5 | 4 | 59 | 0.36 |
| 51 | 1.4 | 0 | — | 6 | 42 | 8 | 11 | 5 | 4 | 70 | 0.36 |

[1] Ac = acetic acid; AA = acrylic acid; MA = maleic acid
[2] STY = Space Time Yield (mmol min$^{-1}$(g or catalyst)$^{-1}$) of MA;

Examples 52–62

Comparative Runs G–H

In another series of n-butane oxidation experiments, flow conditions were varied for a $NbPMo_{12}$V(pyr) based catalyst

TABLE 7

| Ex/ Run | Catalyst | Temp (° C.) | Flow (ml/min) | Conversion (%) C | Conversion (%) O | Selectivity (%)[1] CO | Selectivity (%)[1] $CO_2$ | Selectivity (%)[1] Ac | Selectivity (%)[1] AA | Selectivity (%)[1] MA | STY[2] |
|---|---|---|---|---|---|---|---|---|---|---|---|
| G | VPO | 380 | 4:2:4:5 | 2 | 41 | 14 | 22 | 5 | 2 | 57 | 0.014 |
| H | VPO | 380 | 2:18:77:5 | 0.6 | 2 | — | 59 | 4 | 3 | 34 | $1.4 \times 10^{-3}$ |
| 52 | NMVpr[3] | 300 | 16:8:16:20 | 1.8 | 27 | 11 | 23 | 6 | 2 | 50 | 0.064 |
| 53 | NMVpr[3] | 300 | 16:16:16:20 | 3.7 | 25 | 9 | 17 | 6 | 2 | 61 | 0.14 |
| 54 | NMVpr[3] | 300 | 16:2:16:20 | 2.1 | 62 | 14 | 19 | 17 | 1 | 50 | 0.037 |
| 55 | NMVpr[4] | 300 | 1:10:35:5 | 29 | 33 | 51[5] | | 5 | 1 | 44 | $6.4 \times 10^{-3}$ |
| 56 | NMVpr[4] | 340 | 1:10:35:5 | 62 | 61 | 50[5] | | 4 | 1 | 46 | 0.019 |
| 57 | NMVpr[4] | 340 | 2:10:35:5 | 63 | 81 | 54[5] | | 4 | 1 | 41 | 0.030 |
| 58 | NMVpr[4] | 340 | 8:4:8:10 | 14 | 95 | 24[5] | | 11 | 3 | 62 | 0.14 |
| 59 | NMVpr[4] | 300 | 4:2:4:5 | 9 | 75 | 26[5] | | 12 | 2 | 60 | 0.05 |
| 60 | NMVpr[4] | 420 | 256:128:256:80 | 6.9 | 46 | 22[5] | | 3 | 3 | 68 | 2.37 |
| 61 | NMVpr[4] | 300 | 2:20:76:5 | 3.5 | 5.4 | 0 | 43 | 9 | 2 | 46 | $7.6 \times 10^{-3}$ |
| 62 | (6) | 340 | 32:16:32:40 | 13.5 | 90 | 5[5] | | 4 | 1 | 89 | 0.76 |

[1]Ac = acetic acid; AA = acrylic acid; MA = maleic acid;
[2]STY = Space Time Yield (mmol min$^{-1}$(g or catalyst)$^{-1}$) of MA;
[3]NMVpr = NbMo$_{11}$V(pyr);
[4]0.99 g catalyst;
[5]$CO_x$;
[6]NbPMo$_{12}$(pyr)

Examples 63–68

In another series of experiments, oxidation of n-butane was conducted with catalysts pretreated under varying conditions using the reactor described above. Activation was conducted at 5 ml/min of CO, H$_2$, or NH$_3$ and 45 ml/min of helium using the temperature program described in Example 1. All oxidations were conducted at 380° C. Results are shown in Table 8.

TABLE 8

| Ex/ Run | Catalyst[1] | Pre-treatment | Flow (ml/min) | Conversion (%) C | Conversion (%) O | Selectivity (%)[2] $CO_x$ | Selectivity (%)[2] Ac | Selectivity (%)[2] AA | Selectivity (%)[2] MA | STY[3] |
|---|---|---|---|---|---|---|---|---|---|---|
| 63 | NMV | He | 4:2:4:5 | 0.4 | 8 | 42 | 19 | 4 | 25 | $6.3 \times 10^{-4}$ |
| 64 | NMV | CO | 4:2:4:5 | 11 | 75 | 14 | 12 | 7 | 66 | 0.059 |
| 65 | NMV | NH$_3$ | 4:2:4:5 | 1.4 | 36 | 86 | 2 | — | — | — |
| 66 | NMV | H$_2$ | 4:2:4:5 | 3.4 | 44 | 70 | 9 | 3 | 15 | $7.8 \times 10^{-3}$ |
| 67 | NMVpr | — | 32:16:32:40 | 14 | 95 | 9 | 5 | 3 | 80 | 0.76 |
| 68 | NMVpr | CO | 27:16:32:40 | 12 | 84 | 51 | 5 | 3 | 40 | 0.27 |

[1]NMV = NbPMo$_{11}$V; NMVpr = NbPMo$_{11}$V(pyr)
[2]Ac = acetic acid; AA = acrylic acid; MA = maleic acid
[3]STY = Space Time Yield (mmol min$^{-1}$(g or catalyst)$^{-1}$) of MA;

Examples 69–73

In another series of experiments, isobutane was oxidized using NbPMo$_{11}$V(pyr) as the catalyst precursor and using the activation and reactor conditions described in Example 1. Results are shown in Table 9. In addition, an attempted oxidation using the same catalyst with methane as a feedstock did not detect any conversion at temperatures up to 460° C.

TABLE 9

| Ex/ Run | Alkane Feed[1] | Flow[2] (ml/min) | Conversion (%) C | Conversion (%) O | Selectivity (%)[3] | STY[4] (mmole min$^{-1}$ (g of catalyst)$^{-1}$) |
|---|---|---|---|---|---|---|
| 69 | Iso-C$_4$ | 4:2:4:5 | 15 | 100 | $CO_x$ = 91; Ac = 3.5; AA = 0.5 MAA = 1.4; MA = 2.6 | MAA = $2.3 \times 10^{-3}$ |
| 70 | Iso-C$_4$ | 28:14:28:35 | 13 | 98 | $CO_x$ = 86; Ac = 5.3; AA = 1.3 MAA = 1.7; MA = 3.9 | MAA = 0.013 |

TABLE 9-continued

| Ex/ Run | Alkane Feed[1] | Flow[2] (ml/min) | Conversion (%) C | Conversion (%) O | Selectivity (%)[3] | STY[4] (mmole min$^{-1}$ (g of catalyst)$^{-1}$) |
|---|---|---|---|---|---|---|
| 71 | n-C$_4$ | 32:16:32:40 | 15 | 99 | CO$_x$ = 15; Ac = 9; AA = 6; MA = 75 | MA = 0.85 |
| 72 | Ethane | 4:2:4:5 | 5.7 | 9.6 | C$_2^-$ = 59; Ac = 13 | C$_2^-$ = 3.0 × 10$^{-2}$; Ac = 6.5 × 10$^{-3}$ |
| 73 | Toluene | 0.16:2:4:5 | | | BzA = 8; BA = 29 | BzA = 5.6 × 10$^{-4}$; BA = 2.2 × 10$^{-3}$ |

[1]Iso-C$_4$ = isobutane; n-C$_4$ = n-butane
[2]hydrocarbon/O$_2$/He/H$_2$O molar ratio
[3]Ac = acetic acid; AA = acrylic acid; MA = maleic acid; MAA = methacrylic acid; BzA = benzoic acid; BA = benzaldehyde
[4]Space Time Yield

The invention claimed is:

1. A process of converting a hydrocarbon or a substituted hydrocarbon to a partially oxidized product comprising contacting a hydrocarbon feedstream in the presence of a source of oxygen under partial oxidation conditions with a catalyst comprising an activated polyoxometallate comprising a polyoxoanion containing at least one framework metal bonded through oxygen atoms to at least one heteroatom, which polyoxoanion is charge balanced with at least one partially reduced non-framework metal ion and in which at least one framework metal is partially reduced.

2. A process according to claim 1 wherein a framework metal atom is a Group 5 or 6 atom.

3. A process according to claim 1 wherein a framework metal atom is molybdenum and the heteroatom is phosphorus.

4. A process according to claim 1 wherein the charge balancing metal ion is one or more ions of Group 3–6.

5. A process according to claim 1 wherein the charge balancing metal ion is one or more ions of niobium, titanium, molybdenum, or zirconium.

6. A process according to claim 1 wherein the charge balancing metal ion is niobium ion.

7. A process according to claim 1 wherein the charge balancing metal ion is niobium ion, the framework atom is molybdenum and the heteroatom is phosphorus.

8. A process according to claim 1 wherein the hydrocarbon is ethane, ethylene, propane, propylene, n-butane, 1-butene, or 2-butene.

9. A process of oxidizing a C$_3$ hydrocarbon to a mixture containing acrylic acid comprising contacting a C$_3$ hydrocarbon feedstream in the presence of a source of oxygen under oxidation conditions with an oxidation catalyst comprising an activated polyoxomolybdate charge balanced with niobium ion, in which the niobium ion is partially reduced during activation, wherein a niobium exchanged polyoxomolybdate is activated by heating a pyridinium adduct of the polyoxomolybdate to an effective activation temperature of between 375 and 450° C. in a non-oxidizing atmosphere.

10. A process according to claim 9 wherein the hydrocarbon is propane, propylene, or a mixture thereof.

11. A process of oxidizing a C$_4$ hydrocarbon to a mixture containing maleic acid comprising contacting a C$_4$ hydrocarbon feedstream in the presence of a source of oxygen under oxidation conditions with an oxidation catalyst comprising an activated polyoxomolybdate charge balanced with niobium ion, in which the niobium ion is partially reduced during activation wherein a niobium exchanged polyoxomolybdate is activated by heating a pyridinium adduct of the polyoxomolybdate to an effective activation temperature of between 375 and 450° C. in a non-oxidizing atmosphere.

12. A process according to claim 11 of oxidizing a C$_3$ hydrocarbon to a mixture containing maleic acid comprising contacting a C$_3$ hydrocarbon feedstream in the presence of a source of oxygen under oxidation conditions in which the activated polyoxomolybdate also contains vanadium.

13. A process according to claim 11 wherein the hydrocarbon is n-butane, 1-butene, 2-butene, or a mixture thereof.

14. A process according to claim 12 wherein the hydrocarbon is propane, propylene, or a mixture thereof.

15. A process of oxidizing a C$_2$ hydrocarbon to a mixture containing acetic acid comprising contacting a C$_2$ hydrocarbon feedstream in the presence of a source of oxygen under oxidation conditions with an oxidation catalyst comprising an activated polyoxomolybdate charge balanced with niobium ion, in which the niobium ion is partially reduced during activation wherein a niobium exchanged polyoxomolybdate is activated by heating a pyridinium adduct of the polyoxomolybdate to an effective activation temperature of between 375 and 450° C. in a non-oxidizing atmosphere.

16. A process according to claim 15 wherein the hydrocarbon is ethane, ethylene, or a mixture thereof.

* * * * *